US008328768B2

(12) United States Patent  
Quigley et al.

(10) Patent No.: US 8,328,768 B2  
(45) Date of Patent: Dec. 11, 2012

(54) PRESSURE ACTIVATED SAFETY VALVE WITH IMPROVED FLOW CHARACTERISTICS AND DURABILITY

(75) Inventors: Karla Weaver Quigley, Framingham, MA (US); Paul DiCarlo, Middleboro, MA (US); Mark Wolfson, Wellesley, MA (US)

(73) Assignee: Angiodynamics, Inc, Latham, NY (US)

( * ) Notice: Subject to any disclaimer, the term of this patent is extended or adjusted under 35 U.S.C. 154(b) by 335 days.

(21) Appl. No.: 11/057,286

(22) Filed: Feb. 11, 2005

(65) Prior Publication Data  
US 2006/0184139 A1 Aug. 17, 2006

(51) Int. Cl.  
A61M 5/00 (2006.01)

(52) U.S. Cl. .. 604/246; 604/6.16; 604/533; 604/167.01; 604/167.03; 604/167.04; 604/288.03

(58) Field of Classification Search ............... 604/246, 604/256, 257, 523, 533, 534, 537, 538, 164.01, 604/167.01, 167.03, 288.03, 288.01, 167.04  
See application file for complete search history.

(56) References Cited

U.S. PATENT DOCUMENTS

| | | |
|---|---|---|
| 2,446,571 A | 3/1944 | Browne |
| 2,720,881 A | 10/1955 | Weaver et al. |
| 2,755,060 A | 7/1956 | Twyman |
| 3,113,586 A | 12/1963 | Edmark, Jr. |
| 3,159,175 A | 12/1964 | MacMillan |
| 3,159,176 A | 12/1964 | Russell et al. |
| 3,477,438 A | 11/1969 | Allen et al. |
| 3,514,438 A | 5/1970 | Nelsen et al. |
| 3,525,357 A | 8/1970 | Koreski |
| 3,621,557 A | 11/1971 | Cushman et al. |
| 3,669,323 A | 6/1972 | Harker et al. |
| 3,673,612 A | 7/1972 | Merrill et al. |
| 3,674,183 A | 7/1972 | Venable et al. |
| 3,710,942 A | 1/1973 | Rosenberg |
| 3,788,327 A | 1/1974 | Donowitz et al. |
| 3,811,466 A | 5/1974 | Ohringer |
| 3,941,149 A | 3/1976 | Mittleman |
| 3,955,594 A | 5/1976 | Snow |
| 4,072,146 A | 2/1978 | Howes |
| 4,142,525 A | 3/1979 | Binard et al. |
| 4,143,853 A | 3/1979 | Abramson |
| 4,244,379 A | 1/1981 | Smith |

(Continued)

FOREIGN PATENT DOCUMENTS  
DE 20208420 10/2002  
(Continued)

OTHER PUBLICATIONS

Asch, "Venous access: options, approaches and issues," Can Assoc. Radiol J., vol. 52, No. 3 pp. 153-164 (2001).

(Continued)

Primary Examiner — Quynh-Nhu H Vu  
(74) Attorney, Agent, or Firm — Ryan D. Artis

(57) ABSTRACT

A valve assembly for vascular access, comprising a body defining a lumen adapted for flowing blood, the body including a luer housing for connection with a first blood conduit and a barb housing for connection with a second blood conduit and a plurality of slitted membranes disposed within the body portion, each of the slitted membranes generating a partial pressure drop for flow therethrough, each of the partial pressure drops being smaller than a total pressure drop for flow through the body portion.

10 Claims, 9 Drawing Sheets

U.S. PATENT DOCUMENTS

| | | | |
|---|---|---|---|
| 4,387,879 A * | 6/1983 | Tauschinski | 251/149.1 |
| 4,405,316 A | 9/1983 | Mittleman | |
| 4,434,810 A | 3/1984 | Atkinson | |
| 4,447,237 A | 5/1984 | Frisch et al. | |
| 4,468,224 A | 8/1984 | Enzmann et al. | |
| 4,502,502 A | 3/1985 | Krug | |
| 4,524,805 A | 6/1985 | Hoffman | |
| 4,543,087 A | 9/1985 | Sommercorn et al. | |
| 4,552,553 A | 11/1985 | Schulte et al. | |
| 4,610,665 A | 9/1986 | Matsumoto et al. | |
| 4,616,768 A | 10/1986 | Flier | |
| 4,646,945 A | 3/1987 | Steiner et al. | |
| 4,673,393 A | 6/1987 | Suzuki et al. | |
| 4,681,572 A | 7/1987 | Tokarz et al. | |
| 4,692,146 A | 9/1987 | Hilger | |
| 4,722,725 A | 2/1988 | Sawyer et al. | |
| 4,790,832 A | 12/1988 | Lopez | |
| 4,798,594 A | 1/1989 | Hillstead | |
| 4,801,297 A | 1/1989 | Mueller | |
| 4,908,028 A | 3/1990 | Colon et al. | |
| 4,944,726 A | 7/1990 | Hilal et al. | |
| 4,946,448 A | 8/1990 | Richmond | |
| 4,960,412 A | 10/1990 | Fink | |
| 5,000,745 A * | 3/1991 | Guest et al. | 604/256 |
| 5,009,391 A * | 4/1991 | Steigerwald | 251/149.1 |
| 5,030,210 A | 7/1991 | Alchas et al. | |
| 5,084,015 A | 1/1992 | Moriuchi | |
| 5,098,405 A | 3/1992 | Peterson et al. | |
| 5,125,893 A | 6/1992 | Dryden | |
| 5,147,332 A | 9/1992 | Moorehead | |
| 5,149,327 A | 9/1992 | Oshiyama | |
| 5,167,638 A | 12/1992 | Felix et al. | |
| 5,169,393 A | 12/1992 | Moorehead et al. | |
| 5,176,652 A | 1/1993 | Littrell | |
| 5,176,662 A | 1/1993 | Bartholomew et al. | |
| 5,201,722 A | 4/1993 | Moorehead et al. | |
| 5,205,834 A | 4/1993 | Moorehead et al. | |
| 5,249,598 A | 10/1993 | Schmidt | |
| 5,254,086 A | 10/1993 | Palmer et al. | |
| 5,324,274 A | 6/1994 | Martin | |
| 5,330,424 A | 7/1994 | Palmer et al. | |
| 5,336,203 A | 8/1994 | Goldhardt et al. | |
| 5,360,407 A | 11/1994 | Leonard et al. | |
| 5,370,624 A | 12/1994 | Edwards et al. | |
| 5,395,352 A | 3/1995 | Penny | |
| 5,396,925 A | 3/1995 | Poli et al. | |
| 5,399,168 A | 3/1995 | Wadsworth et al. | |
| 5,401,255 A | 3/1995 | Sutherland et al. | |
| D357,735 S | 4/1995 | McPhee | |
| 5,405,340 A | 4/1995 | Fageol et al. | |
| 5,411,491 A | 5/1995 | Goldhardt et al. | |
| 5,453,097 A | 9/1995 | Paradis | |
| 5,454,784 A | 10/1995 | Atkinson et al. | |
| 5,469,805 A | 11/1995 | Gibbs et al. | |
| 5,470,305 A | 11/1995 | Arnett et al. | |
| 5,484,420 A | 1/1996 | Russo | |
| 5,542,923 A | 8/1996 | Ensminger et al. | |
| 5,545,150 A * | 8/1996 | Danks et al. | 604/256 |
| 5,554,136 A | 9/1996 | Luther | |
| 5,562,618 A | 10/1996 | Cai et al. | |
| 5,571,093 A | 11/1996 | Cruz et al. | |
| 5,575,769 A | 11/1996 | Vaillancourt et al. | |
| 5,624,395 A | 4/1997 | Mikhail et al. | |
| 5,637,099 A | 6/1997 | Durdin et al. | |
| 5,667,500 A | 9/1997 | Palmer et al. | |
| 5,707,357 A | 1/1998 | Mikhail et al. | |
| 5,743,873 A | 4/1998 | Cai et al. | |
| 5,743,884 A | 4/1998 | Hasson et al. | |
| 5,743,894 A | 4/1998 | Swisher | |
| 5,752,938 A | 5/1998 | Flatland et al. | |
| 5,803,078 A | 9/1998 | Brauner | |
| 5,807,349 A | 9/1998 | Person et al. | |
| 5,810,789 A | 9/1998 | Powers et al. | |
| 5,843,044 A | 12/1998 | Moorehead | |
| 5,853,397 A | 12/1998 | Shemesh et al. | |
| 5,865,308 A | 2/1999 | Qin et al. | |
| 5,944,698 A | 8/1999 | Fischer et al. | |
| 5,984,902 A | 11/1999 | Moorehead | |
| 5,989,233 A | 11/1999 | Yoon | |
| 6,033,393 A | 3/2000 | Balbierz et al. | |
| 6,045,734 A | 4/2000 | Luther et al. | |
| 6,050,934 A | 4/2000 | Mikhail et al. | |
| 6,056,717 A | 5/2000 | Finch et al. | |
| 6,062,244 A | 5/2000 | Arkans | |
| 6,092,551 A | 7/2000 | Bennett | |
| 6,099,505 A | 8/2000 | Ryan et al. | |
| 6,120,483 A | 9/2000 | Davey et al. | |
| 6,152,909 A | 11/2000 | Bagaoisan et al. | |
| 6,210,366 B1 | 4/2001 | Sanfilippo | |
| 6,227,200 B1 | 5/2001 | Crump et al. | |
| 6,270,489 B1 | 8/2001 | Wise et al. | |
| 6,306,124 B1 | 10/2001 | Jones et al. | |
| 6,364,861 B1 | 4/2002 | Feith et al. | |
| 6,364,867 B2 | 4/2002 | Wise et al. | |
| 6,375,637 B1 | 4/2002 | Campbell et al. | |
| 6,436,077 B1 | 8/2002 | Davey et al. | |
| 6,442,415 B1 | 8/2002 | Bis et al. | |
| 6,446,671 B2 | 9/2002 | Armenia et al. | |
| 6,508,791 B1 | 1/2003 | Guerrero | |
| 6,551,270 B1 | 4/2003 | Bimbo et al. | |
| 6,610,031 B1 | 8/2003 | Chin | |
| 6,726,063 B2 | 4/2004 | Stull et al. | |
| 6,786,884 B1 | 9/2004 | DeCant et al. | |
| 6,874,999 B2 | 4/2005 | Dai et al. | |
| 6,953,450 B2 | 10/2005 | Baldwin et al. | |
| 6,994,314 B2 | 2/2006 | Garnier et al. | |
| 7,081,106 B1 * | 7/2006 | Guo et al. | 604/167.06 |
| 7,252,652 B2 | 8/2007 | Moorehead et al. | |
| 7,291,133 B1 | 11/2007 | Kindler et al. | |
| 7,316,655 B2 | 1/2008 | Garibotto et al. | |
| 7,435,236 B2 | 10/2008 | Weaver et al. | |
| 7,601,141 B2 | 10/2009 | Dikeman et al. | |
| 7,637,893 B2 | 12/2009 | Christensen et al. | |
| 7,758,541 B2 | 7/2010 | Wallace et al. | |
| 2001/0023333 A1 | 9/2001 | Wisse et al. | |
| 2001/0037079 A1 | 11/2001 | Burbank et al. | |
| 2002/0010425 A1 | 1/2002 | Guo et al. | |
| 2002/0016584 A1 | 2/2002 | Wise et al. | |
| 2002/0121530 A1 | 9/2002 | Socier | |
| 2002/0156430 A1 | 10/2002 | Haarala et al. | |
| 2002/0165492 A1 | 11/2002 | Davey et al. | |
| 2002/0193752 A1 | 12/2002 | Lynn | |
| 2003/0122095 A1 | 7/2003 | Wilson et al. | |
| 2004/0034324 A1 | 2/2004 | Seese et al. | |
| 2004/0064128 A1 | 4/2004 | Raijman et al. | |
| 2004/0102738 A1 | 5/2004 | Dikeman | |
| 2004/0108479 A1 | 6/2004 | Garnier et al. | |
| 2004/0186444 A1 | 9/2004 | Daly et al. | |
| 2004/0193119 A1 | 9/2004 | Canaud et al. | |
| 2004/0210194 A1 * | 10/2004 | Bonnette et al. | 604/167.06 |
| 2004/0267185 A1 | 12/2004 | Weaver et al. | |
| 2005/0004955 A1 | 1/2005 | Lee et al. | |
| 2005/0010176 A1 | 1/2005 | Dikeman et al. | |
| 2005/0027261 A1 | 2/2005 | Weaver et al. | |
| 2005/0043703 A1 | 2/2005 | Nordgren | |
| 2005/0049555 A1 * | 3/2005 | Moorehead et al. | 604/122 |
| 2005/0149116 A1 | 7/2005 | Edwards et al. | |
| 2005/0171490 A1 | 8/2005 | Weaver et al. | |
| 2005/0171510 A1 | 8/2005 | DiCarlo et al. | |
| 2005/0283122 A1 | 12/2005 | Nordgren | |
| 2006/0129092 A1 | 6/2006 | Hanlon et al. | |
| 2006/0135949 A1 | 6/2006 | Rome et al. | |
| 2006/0149211 A1 | 7/2006 | Simpson et al. | |
| 2007/0161940 A1 | 7/2007 | Blanchard et al. | |
| 2007/0161970 A1 | 7/2007 | Spohn et al. | |
| 2007/0276313 A1 | 11/2007 | Moorehead et al. | |
| 2008/0108956 A1 | 5/2008 | Lynn et al. | |
| 2009/0292252 A1 | 11/2009 | Lareau et al. | |

FOREIGN PATENT DOCUMENTS

| | | |
|---|---|---|
| EP | 0128525 | 12/1984 |
| EP | 0337617 | 10/1989 |
| EP | 0474069 | 3/1992 |
| EP | 0864336 | 9/1998 |
| EP | 0930082 | 7/1999 |
| EP | 1016431 | 7/2000 |
| FR | 2508008 | 12/1982 |

| | | |
|---|---|---|
| FR | 2718969 | 10/1995 |
| GB | 966137 | 8/1964 |
| GB | 2102398 | 2/1983 |
| JP | 59133877 | 8/1984 |
| JP | 63255057 | 10/1988 |
| JP | 9038197 | 2/1997 |
| WO | WO-89/02764 | 4/1989 |
| WO | 92/06732 | 4/1992 |
| WO | 95/16480 | 6/1995 |
| WO | WO-96/17190 | 6/1996 |
| WO | WO-96/23158 | 8/1996 |
| WO | WO-96/41649 | 12/1996 |
| WO | 97/23255 | 7/1997 |
| WO | 97/26831 | 7/1997 |
| WO | WO-98/22178 | 5/1998 |
| WO | 99/42166 | 8/1999 |
| WO | WO-00/06230 | 2/2000 |
| WO | 00/44419 | 8/2000 |
| WO | WO-01/74434 | 10/2001 |
| WO | 03/084832 | 10/2003 |
| WO | 2005/023355 | 3/2005 |
| WO | WO-2008/089985 | 7/2008 |

OTHER PUBLICATIONS

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahous et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

Examination Report mailed Jun. 6, 2008 for European Patent Application No. 05852275.6 (3 pages).

Examination Report mailed May 15, 2009 for European Patent Application No. 05852275.6 (4 pages).

Office Action mailed Apr. 12, 2012 for Canadian Patent Application No. 2,597,505 (2 pages).

International Search Report and Written Opinion mailed Apr. 28, 2006 for International Application No. PCT/US2005/042909 (10 pages).

International Preliminary Report on Patentability mailed Aug. 14, 2007 for International Application No. PCT/US2005/042909 (7 pages).

\* cited by examiner

PRESSURE ACTIVATED SAFETY VALVE WITH IMPROVED FLOW CHARACTERISTICS AND DURABILITY

The present application incorporates by reference entire disclosure of (1) U.S. application Ser. No. 10/768,571 entitled "Pressure Activated Safety Valve with Anti-adherent Coating" filed on Jan. 29, 2004 naming Karla Weaver and Paul DiCarlo as inventors; (2) U.S. application Ser. No. 10/768,565 entitled "Pressure Activated Safety Valve with High Flow Slit" filed on Jan. 29, 2004 naming Karla Weaver and Paul DiCarlo as inventors; (3) U.S. application Ser. No. 10/768,629 entitled "Stacked Membrane For Pressure Actuated Valve" filed on Jan. 29, 2004 naming Karla Weaver and Paul DiCarlo as inventors; (4) U.S. application Ser. No. 10/768,855 entitled "Pressure Actuated Safety Valve With Spiral Flow Membrane" filed on Jan. 29, 2004 naming Karla Weaver and Paul DiCarlo as inventors; and (5) U.S. application Ser. No. 10/768,479 entitled "Dual Well Port Device" filed on Jan. 29, 2004 naming Katie Daly, Kristian DiMatteo and Eric Houde as inventors.

BACKGROUND OF THE INVENTION

Many medical procedures require repeated and prolonged access to a patient's vascular system. For example, during dialysis treatment blood may be removed from the body for external filtering and purification, to make up for the inability of the patient's kidneys to carry out that function. In this process, the patient's venous blood is extracted, processed in a dialysis machine and returned to the patient. The dialysis machine purifies the blood by diffusing harmful compounds through membranes, and may add to the blood therapeutic agents, nutrients etc., as required before returning it to the patient's body. Typically the blood is extracted from a source vein (e.g., the vena cava) through a catheter sutured to the skin with a distal needle of the catheter penetrating the source vein.

It is impractical and dangerous to insert and remove the catheter for each dialysis session. Thus, the needle and catheter are generally implanted semi permanently with a distal portion of the assembly remaining within the patient in contact with the vascular system while a proximal portion of the catheter remains external to the patient's body. The proximal end is sealed after each dialysis session has been completed to prevent blood loss and infections. However, even small amounts of blood oozing into the proximal end of the catheter may be dangerous, as thrombi can form therein due to coagulation. These thrombi may then be introduced into the patient's vascular system when blood flows from the dialysis machine through the catheter in a later session.

A common method of sealing the catheter after a dialysis session is to shut the catheter with a simple clamp. This method is often unsatisfactory because the repeated application of the clamp may weaken the walls of the catheter due to the stress placed on the walls at a single point. In addition, the pinched area of the catheter may not be completely sealed allowing air to enter the catheter which may coagulate any blood present within the catheter. Alternatively, valves have been used at the opening of the catheter in an attempt to prevent leaking through the catheter when the dialysis machine is disconnected. However, the unreliability of conventional valves has rendered them unsatisfactory for extended use.

The effect of the presence of valves within the flow of blood may cause some potentially harmful effects. When a fluid passes through a restriction such as the valve, its velocity increases and its pressure decreases. If the decrease in pressure is sufficiently large, the pressure may fall below the vapor pressure of the fluid, causing the formation of gas bubbles. The formation of bubbles, or cavitation, in blood flowing through the vascular system may be dangerous to the patient, because the gas bubbles may become trapped in a blood vessel and may impede flow of blood therethrough. Flow recirculation within the valve also may cause deposits of biological material to form in the passages, which also may leave the valve and become lodged in a blood vessel, impeding passage of blood. The recirculation within the valve may also cause damage to the blood cells which pass through the valve.

SUMMARY OF THE INVENTION

In one aspect, the present invention is directed to a valve assembly for vascular access, comprising a body defining a lumen adapted for flowing blood, the body including a luer housing for connection with a first blood conduit and a barb housing for connection with a second blood conduit and a plurality of slitted membranes disposed within the body portion, each of the slitted membranes generating a partial pressure drop for flow therethrough, each of the partial pressure drops being smaller than a total pressure drop for flow through the body portion.

The present invention is further directed to a valve assembly for vascular access, comprising a slitted membrane extending across a passage through the valve assembly to selectively block flow of blood therethrough and a luer housing at a first end of the passage for connection with a first blood conduit, a tapered section of the luer housing having a taper angle of between about 125 degrees and about 173 degrees in combination with a barb housing at a second end of the passage for connection with a second blood conduit.

DETAILED DESCRIPTION

Figure 1:
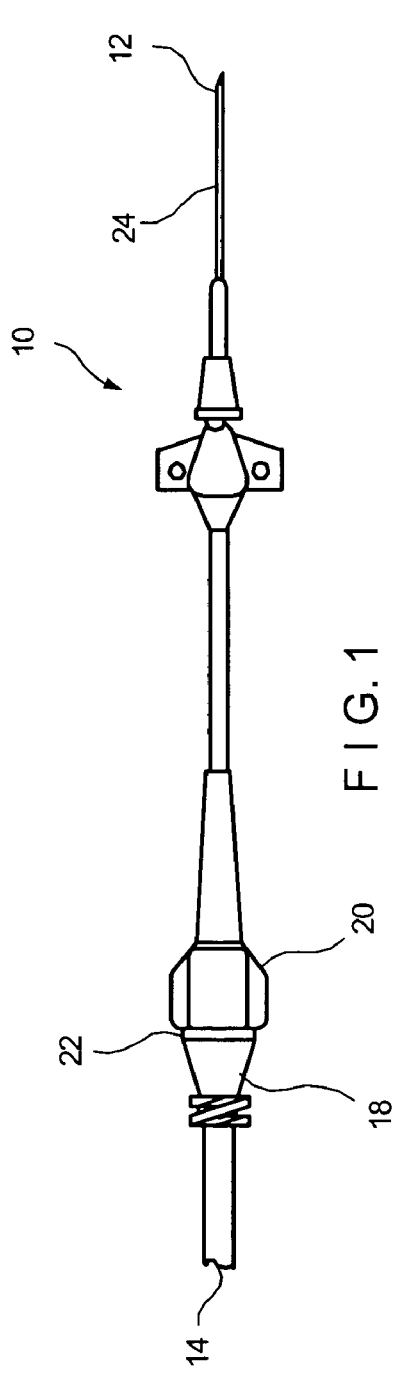
FIG. 1 is a schematic diagram showing a dialysis catheter including a valve according to an embodiment of the present invention.

The present invention may be further understood with reference to the following description and the appended drawings, wherein like elements are referred to with the same reference numerals. The present invention is related to medical devices that are used to access the vascular system of a patient, and in particular to pressure activated safety valves used in kidney dialysis catheters. It will be apparent to those of skill in the art that the present invention may be adapted for use in other medical access devices.

Semi-permanently placed catheters may be useful for a variety of medical procedures which require repeated access to a patient's vascular system in addition to the dialysis treatments mentioned above. For example, kidney dialysis may be repeated on a regular basis for extended periods of time. For safety reasons, as well as to improve the comfort of the patient, access to the patient's vascular system may be better carried out with an implantable, semi-permanent vascular access catheter. Many other conditions that require chronic venous supply of therapeutic agents, nutrients, blood products or other fluids to the patient may also benefit from implantable access catheters, to avoid repeated insertion of a needle into the patient's blood vessels. Thus, although the following description focuses on dialysis, those skilled in the art will understand that the invention may be used in conjunction with any of a wide variety of procedures which require long term implantation of catheters within the body.

Examples of such implantable catheters include those manufactured by Vaxcel™, such as the Chronic Dialysis Catheter and the Implantable Vascular Access System. These devices typically are inserted under the patient's skin, and have a distal end which includes a needle used to enter a blood vessel. The devices also have a proximal end extending outside the body for connection with an outside line. These semi-permanent catheters may be sutured to the patient's skin to maintain them in place while the patient goes about his or her normal occupations. In other cases, the catheter may be less permanent, and may only be implanted in the patient for limited periods of time.

FIG. 1 shows an exemplary catheter such as, for example, the Vaxcel™ Chronic Dialysis Catheter. The catheter 10 has a distal end 12 that is insertable into a patient's vein, and which remains within the patient's body for the duration of use of the catheter 10. The distal end 12 includes a needle (not shown) that pierces the vein of the patient to reach the flow of blood. During dialysis, blood from the patient is removed, for example through the catheter 10, and is purified by a dialysis machine (not shown) which is connected to a hub 18 of the catheter 10 via an external line 14. The catheter 10 may include two or more lumens with a first one of the lumens being used to remove blood from the blood vessel and a second one of the lumens being used to reintroduced treated blood and/or therapeutic agents into the blood vessel. As described above, in addition to dialysis, devices similar to the catheter 10 may be used to access a patient's vascular system for other types of treatment, for example to infuse chemotherapy agents or other medications, to supply food and to remove blood samples.

When disconnected from the dialysis machine, the catheter 10 remains within the patient, connected to the patient's vascular system. Thus, it is important to securely seal the hub 18 to prevent fluids from escaping therefrom and contaminants from entering the patient's body. For example, although the proximal end of the catheter 10 may be clamped to close it off, if an effective seal is not obtained, the patient runs a serious risk of infection as well as risks of embolisms due to air entering the blood stream. Another risk is that of venous thrombosis, which is due to coagulation of blood in and near the catheter. In addition, leakage from an improperly sealed catheter may expose attending medical staff to a risk of infection by blood borne pathogens. Thus a mechanism is necessary to ensure that the catheter 10 is sealed when not in use.

Conventional clamps or clips have been used to seal medical tubes such as catheter 10 between medical sessions. However, as the sealing forces repeatedly applied by these clips are exerted on a small portion of the surface area of the catheter 10, damage to the wall of the catheter 10 at this portion can significantly reduce the effective life of the catheter 10. It is also desirable to improve the resistance of a sealing mechanism for the catheter 10 to forces applied during activities of the patient, so that the sealing mechanism will remain effective without restricting the activity of the patient. Finally, it is desirable to minimize the bulk of the sealing mechanism to enhance patient comfort.

An alternative to clamping or clipping the catheter 10 is to include self sealing valves near the entrance of the flow passages of the catheter, to seal those passages when not in use. For example, the hub 18 may house one or more valve assemblies 20 which are designed to seal the lumen(s) of the catheter 10 under certain conditions, and to allow passage of fluid therethrough under other conditions. In an exemplary case applicable to a dialysis catheter, the system of valves may seal the catheter 10 when it is not connected to an operating dialysis machine, and may allow both an outflow of non-purified blood and an inflow of purified blood to the patient when an operating dialysis machine is connected thereto. These valve assemblies 20 thus selectively allow flow into or out of the patient only under predetermined conditions when they are placed in fluid contact with the inflow or outflow portions of a dialysis catheter 10. For example, the valve 22 may be located between a patient vascular line 24 which is in fluid connection with the patient's vascular system, and the external line 14, which is connectable to the dialysis machine.

Pressure activated safety valves (PASV's) are one type of flow control device that has been used to seal vascular catheters when not in use. These valves open when subject to flow pressure of at least a pre-determined threshold value and remain closed when subject to flow pressures below the pre-determined threshold value. In the exemplary case of a PASV used in a dialysis catheter, the valve is preferably designed so that the pre-determined pressure substantially exceeds a pressure to which the valve would be subjected from the vascular system or due to patient activity. The pre-determined threshold pressure may correspond to a pressure approximating a lower level of the pressures to which the valve would be subjected by an operating dialysis machine. Thus, when no dialysis machine is connected to the catheter, the pressure in the lumen is insufficient to open the PASV, and the catheter remains sealed.

A typical PASV comprises an housing through which the flow of a liquid passes from an inlet portion to an outlet portion. A slitted membrane is disposed within the housing, generally perpendicular to the direction of flow. The slitted membrane is the flow control element of the valve, and may be formed of an elastic material which can deform to a certain extent under the pressure of the fluid. The material, however, is sufficiently resilient so that the slit remain substantially closed unless a pressure above a selected threshold pressure is applied to the membrane by the fluid. In that configuration, the membrane is closed and no fluid can flow through the membrane, thus through the valve. If the fluid pressure rises above the threshold value, the resilience of the membrane material is overcome, and the slit opens. In this open configuration, the fluid is allowed through the membrane and thus through the valve. The threshold pressure may be selected to be below a pressure applied to the fluid by an operating dialysis machine, but well above a pressure normally existing in a vascular system.

Figure 2:
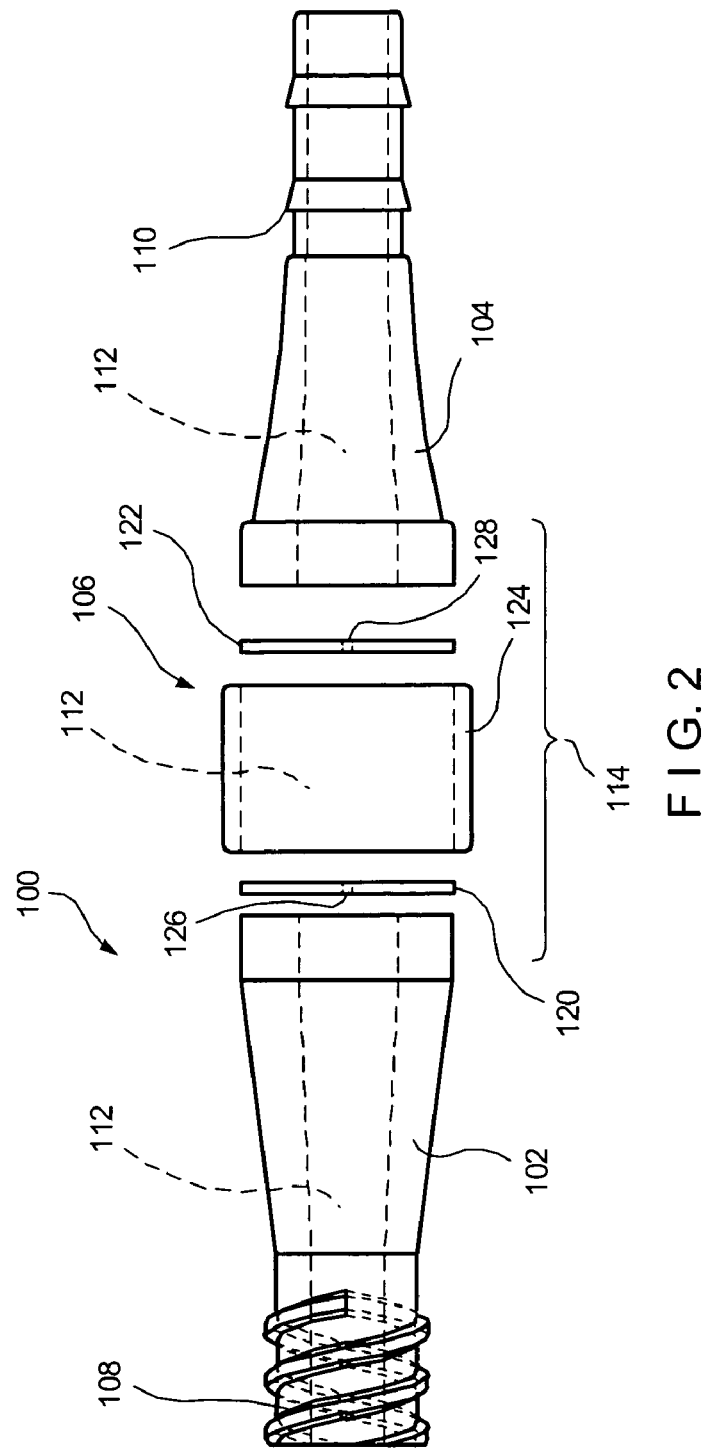
FIG. 2 is a side elevation view showing an embodiment of a pressure activated safety valve according to the present invention.

Due to the design of conventional PASV slitted membranes, the fluid (typically blood) is accelerated while passing through the orifice formed by the slit of the membrane. According to Bernoulli's equation, the pressure of the fluid is inversely proportional to the fluid's velocity, thus the fluid pressure drops through the slit as its velocity increases through the narrow orifice. The velocity reaches a minimum value at a point called the vena contracta. If the pressure of the fluid falls below its vapor pressure, some of the gases contained in the liquid (i.e. blood) may come out of solution, and form gas bubbles within the liquid. These bubbles may cause serious problems in blood, because they may travel through the patient's vascular system and may become lodged in a blood vessel, which as a result may be totally or partially blocked. In addition, the formation of bubbles may interfere with the flow of blood through the valve, reducing the device's performance The problems described above may be alleviated by utilizing a pressure control element built into the valve to manage the pressure of the fluid flowing therethrough. FIG. 2 shows an exemplary embodiment of a PASV according to the present invention, which includes a pressure control element. Valve 100 comprises a body portion 106 which defines a flow passage or lumen 112 through which the fluid passes. A luer housing 102 is disposed at one end of the body portion 106, and includes a luer connector 108 adapted for connection with a fluid conduit, for example attached to a dialysis machine. A barb housing 104 is disposed at the opposite end of the body portion 106. A connector 110 may be formed on the barb housing 104, to couple with a second blood conduit, for example a patient line leading to the patient's vascular system. A pressure control element 114 may comprise several portions of the valve 100, as necessary to control the pressure variation of the flow of blood through the devoice. The design of the pressure control element 114 is selected to control a shape of the pressure profile of the flow passing through the valve 100.

In one exemplary embodiment, the pressure drop across the valve 100 is managed by providing the PASV with multiple slitted membranes rather than one single membrane, as is done conventionally. As shown in FIG. 2, a first membrane 120 and a second membrane 122 may be disposed in body portion 106, separated by a midsection housing 124. Each of the membranes 120, 122 has a corresponding slit 126, 128 which is normally closed, but which opens when the flow pressure is above the threshold pressure. In this manner, the total required pressure drop caused by passing the fluid through a restriction is absorbed across the multiple membranes in multiple steps, rather than across only one membrane. Each individual membrane 120, 122 thus causes a partial pressure drop in the fluid, which is smaller than would be the case if a single membrane was used to selectively block the flow.

In the exemplary embodiment depicted there are two membranes 120, 122 that prevent flow of fluid through the valve 100. As a result, each of the membranes may have a smaller modulus or may be thinner, so that it is more easily openable. Accordingly, each of membranes 120 and 122 may require a lower pressure to open fully, causes a smaller pressure drop, and thus results in a smaller increase in velocity of the fluid flowing through the corresponding slits 126, 128. For example, flow entering the valve 100 through the luer housing 102 initially encounters first slitted membrane 120. If the pressure of the fluid is below the threshold pressure for the valve 100, the fluid will not pass through the complete valve 100. This case corresponds to the situation where the dialysis machine is not connected to the catheter.

Since the first membrane 120 has less resistance to opening than a corresponding single flow control membrane, some of the fluid may pass through the slit 126. However, since there is more than one membrane in the valve 100, the small amount of flow which passes through membrane 120 into the midsection housing 124 can be completely retained by the second membrane 122. The pressure of the fluid in midsection housing 124 is further reduced by the passage through slit 126. The second slitted membrane 122 will then easily prevent further flow of the fluid, since the pressure of the fluid in midsection housing 124 is insufficient to open slit 128.

In the case where the luer housing 102 is connected to an operating dialysis machine, the flow entering the valve 100 will be at a pressure above the valve's threshold pressure. Both slits 126, 128 of slitted membranes 120, 122 will then open under that pressure and will let the fluid pass. However, since each slitted membrane 120, 122 absorbs only a partial pressure drop, lower than the total pressure drop across the valve 100, the pressure of the blood is never reduced to the vapor pressure. The blood flowing through valve 100 thus does not experience cavitation. In the exemplary embodiment shown in FIG. 2, the first and second membranes 121, 122 are placed between the midsection housing 124 and the luer housing 102 and the barb housing 104, respectively. It will be apparent to those skilled in the art that the slitted membranes may be placed at different locations within the body portion 106, as determined by usage and assembly requirements. It will also be apparent that more than two slitted membranes may be used in valve 100.

Figure 3:
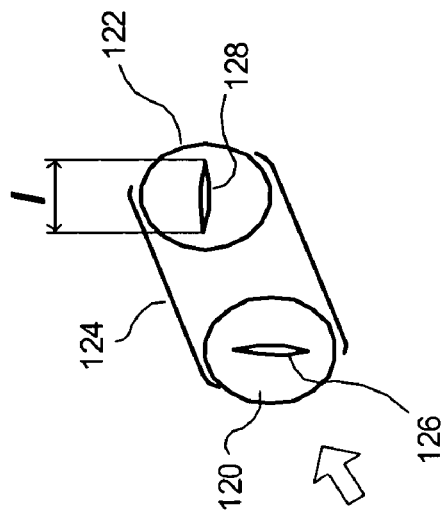
FIG. 3 is a perspective view showing two offset slitted membranes according to an embodiment of the present invention.

As indicated above, the pressure decrease in the blood is related to the increase in velocity through the valve 100. To further reduce the pressure drop, it is beneficial to introduce in the design of valve 100 additional features adapted to reduce the flow velocity in the housing rather than across the slitted membranes. For example, the orientation of the slits 126, 128 may be selected to further reduce the blood velocity in midsection housing 124. In one exemplary embodiment depicted in FIG. 3, the slits 126. 128 have an orientation which is offset by approximately 90 degrees from one another. In this manner, the flow of blood passing through slit 126 has to change direction to pass through slit 128. This change in direction of the fluid requires energy, which is taken from the kinetic energy of the fluid, and causes a reduction in the fluid velocity. The pressure drop across the second slit is therefore reduced further.

In addition or instead of orienting successive slitted membranes in a staggered configuration, the velocity of the blood flow may also be reduced by using different slit configurations on the membranes. For example, membrane 120 may be formed with a linear slit 126, while membrane 122 may be formed with an S-shaped slit. In this case too, the flow of blood has to change direction to pass from one slitted membrane to the other, which further reduces the flow's velocity and maintains a higher pressure of the flow.

Figure 11:
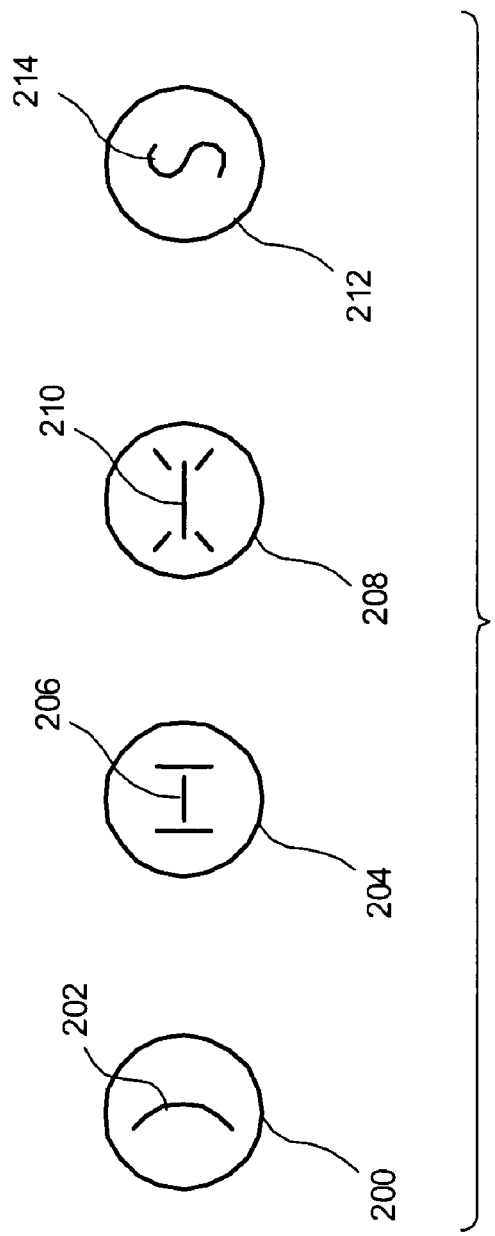
FIG. 11 is a diagram showing several slit configurations according to the present invention.

FIG. 11 shows some exemplary configurations of slitted membranes which may be used in place of one or both of slitted membranes 120, 122. Slitted membrane 200 comprises a single radius slit 202 which extends along a circular path, providing a larger opening than a comparable linear slit. Membrane 204 comprises a plurality of slits disposed in an H-shaped configuration 206. The H-shaped configuration also permits a larger amount of fluid to flow through the membrane 204 in the open configuration. Membrane 208 comprises a Y-shaped pattern 210 of several slits. Membrane 212 includes a single S-shaped slit 214, which in the open configuration provides a greater open flow area than a linear slit. However, the ability of the non-linear slits to close against a flow pressure may be less than that of a comparable membrane with a linear slit. Various combinations of one or more types of slits may be included in one membrane, to obtain the desired open flow area and closure ability.

The larger the flow area available for the flow of blood, the lower the fluid velocity tends to be. Accordingly, it may be beneficial to increase the size of the slits in the flow control membrane(s) of valve 100, and/or to increase the size of the body portion 106, particularly near the slitted membranes. In one exemplary embodiment, the membranes 120, 122 may be thinner than a comparable single membrane, so that a larger opening may be obtained from the slits 126, 128 in the open configuration, for a given flow pressure. As described above, two membranes which are more easily opened than a single membrane can still be capable of remaining closed when the flow pressure is below the valve's threshold pressure. An increase in the length "l" of the slits 126, 128 can achieve the same result. The thickness and slit length "l" of the membranes 120, 122 may thus be selected to obtain a desired minimum flow area of the slits 126, 128, in the open configuration. An increase in dimensions of the midsection housing 124, and/or of the barb and luer housings 102, 104 may also be used to accommodate the longer slits of the membranes.

Figure 6:
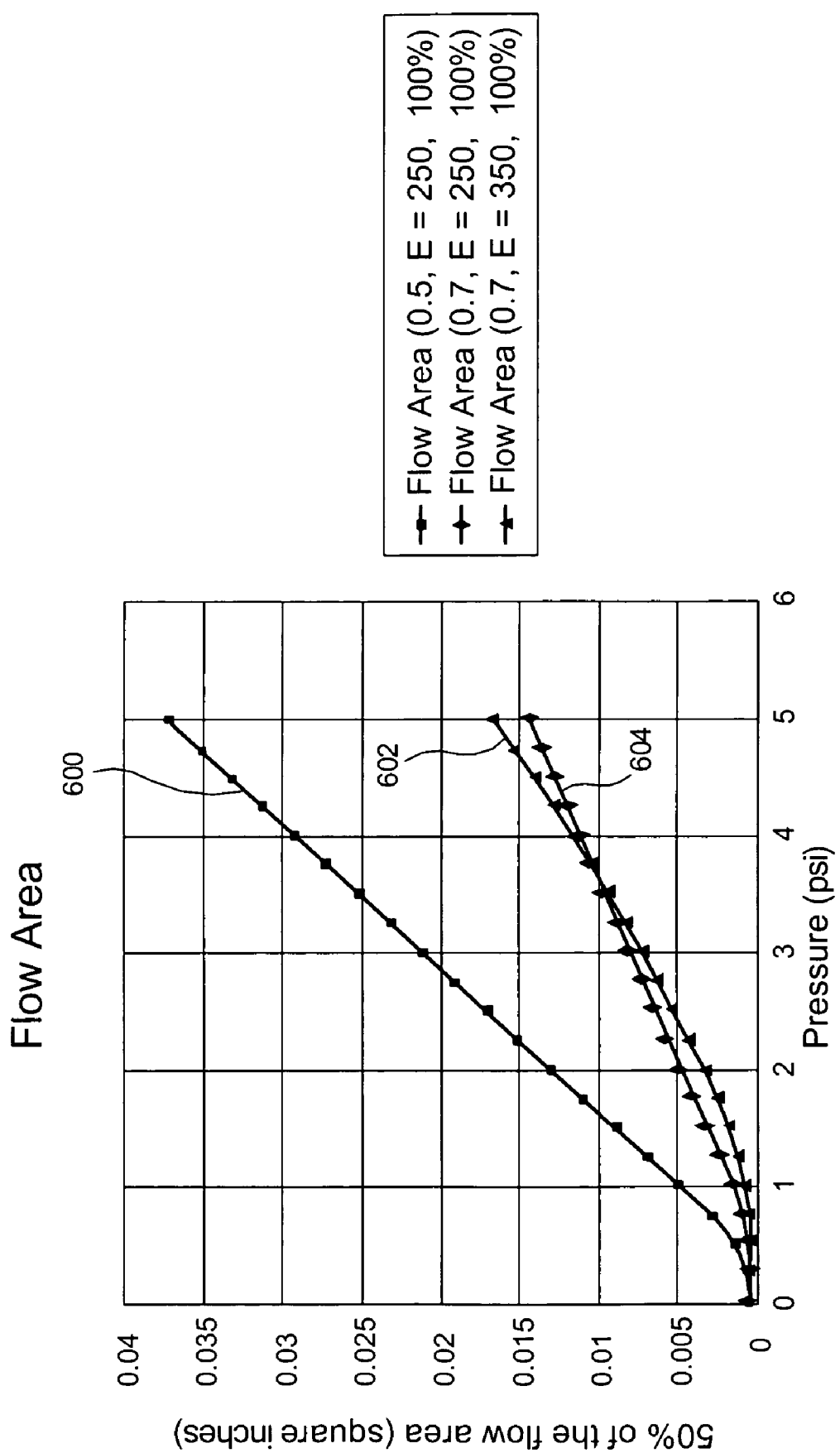
FIG. 6 is a plot of pressure vs. flow area for valves according to the present invention.

In an exemplary embodiment, the length of the slit(s) 126, 128 may be increased from a conventional value of about 6.6 mm to about 9.0 mm, resulting in an increase in flow area in the open configuration of about 150%. In another exemplary embodiment, a reduction in the thickness and/or the modulus of one or all the slitted membranes 120, 122 used in valve 100 may provide an increase of flow area of about 130%. FIG. 6 shows a graph of the flow area plotted against the flow pressure for various configurations. Line 600 represents the flow area as a function of pressure for a valve having a slitted membrane of 0.016 inches thickness, a modulus of 250 PSI and a 9 mm long slit. Line 602 represents the flow area of a slitted membrane 0.020 inches thick, with a 350 PSI modulus and a 9 mm long slit. Line 604 is for a 0.016 inches thick membrane with a 250 PSI modulus and a 6.6 mm long slit.

Figure 4:
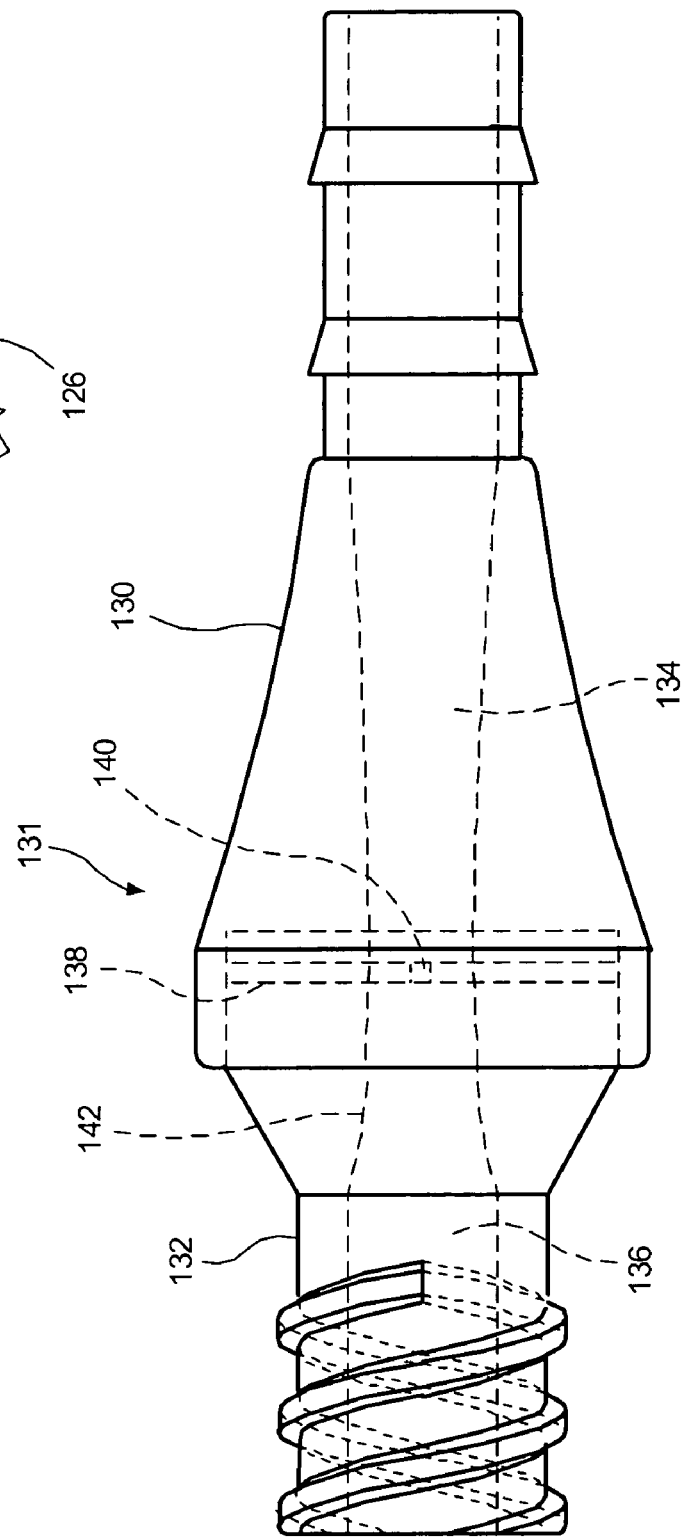
FIG. 4 is a side elevation view showing a second embodiment of a pressure activated safety valve according to the present invention.

FIG. 4 shows another exemplary embodiment of the present invention. In this embodiment, the luer housing 132 and the barb housing 130 are connected directly, and only one slitted membrane is used. A flow passage 136 defined by the luer housing 132 is in fluid connection with a flow passage 134 of the barb housing 130. Flow passages 134 and 136 are designed to direct the flow of blood towards the slit 140 in slitted membrane 138. Directing the flow in alignment with the slit 140 minimizes the change in velocity of the fluid, because in the open configuration most of the fluid flows directly to the open slit 140 of the slitted membrane 138, and is not slowed down locally before reaching the open slit 140. In the exemplary embodiment, the flow enters the valve 131 from the luer housing 132. Accordingly, the inner surface 142 of the flow passage 136 is shaped to direct the fluid to slit 140. The flow passage 136 thus may have a squashed, oval or elliptic cross section with a major axis aligned with the length of the slit 140. In other embodiments, either or both of flow passages 134, 136 may follow a contoured flow path aligned with the slitted membrane, depending on the direction of the fluid flow.

Figure 5:
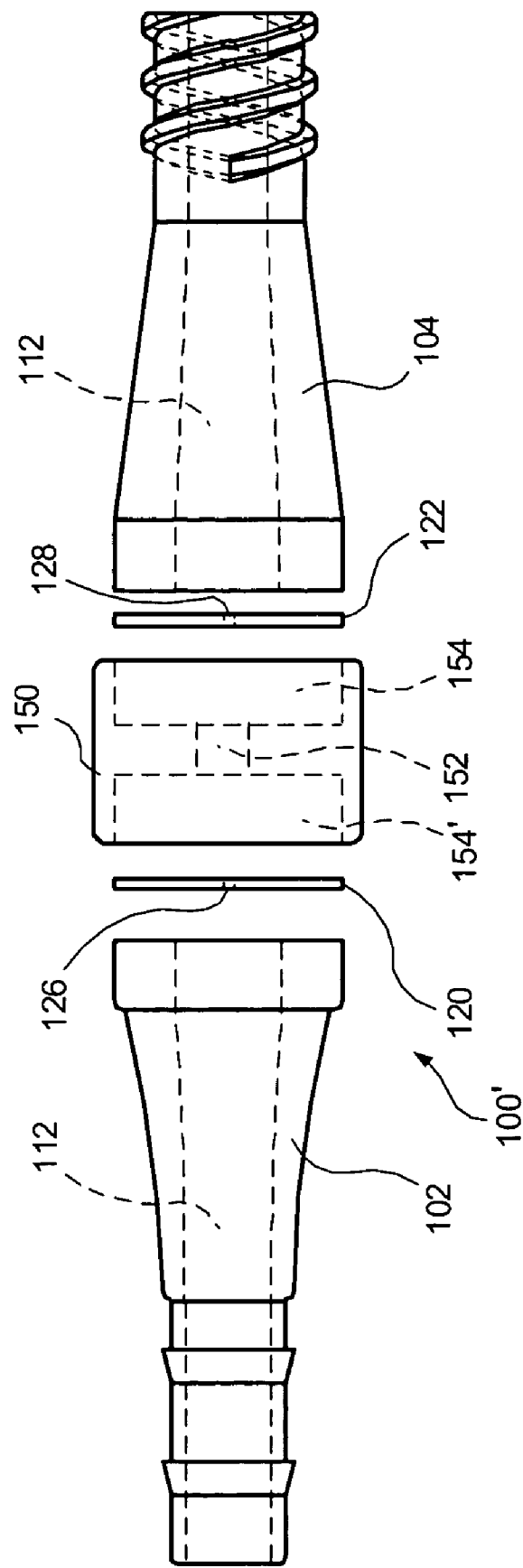
FIG. 5 is a side elevation view showing a third embodiment of a pressure activated safety valve according to the present invention.

Another exemplary embodiment having more than one slitted membrane, according to the present invention, is shown in FIG. 5. In this embodiment, the flow is directed towards the slits 126, 128 of the membranes 120, 122 by the midsection housing 150. The flow passages 152, 154 cooperate to direct the flow of blood to both slits 126, 128, and thus to minimize the change in velocity through the device. As described above, minimizing the change in velocity of the fluid also results in minimizing the pressure drop, thus preventing the formation of gas bubbles in the blood. The flow passages 112 in the luer housing 104 and barb housing 102 may also be contoured as described above, to better control the flow through the valve.

Figure 12:
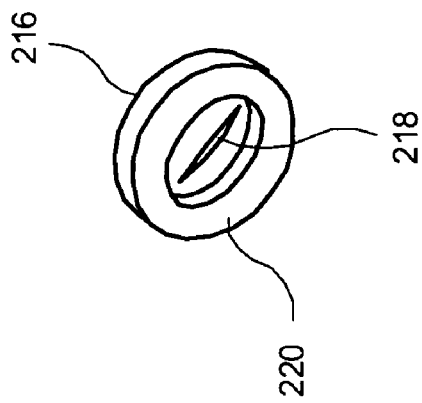
FIG. 12 is a diagram showing a beveled slitted membrane according to the present invention.

Another embodiment according to the present invention comprises one or more slitted membranes which are also beveled or otherwise sculpted to direct the flow towards the slit. For example, the slitted membrane 216 shown in FIG. 12 comprises a beveled surface 220 which is designed to direct a flow of fluid, such as blood, towards slit 218. In a manner analogous to that described above, directing the flow towards the slit 218 reduces the change in velocity and the pressure drop of the fluid across the membrane 216.

Figure 7:
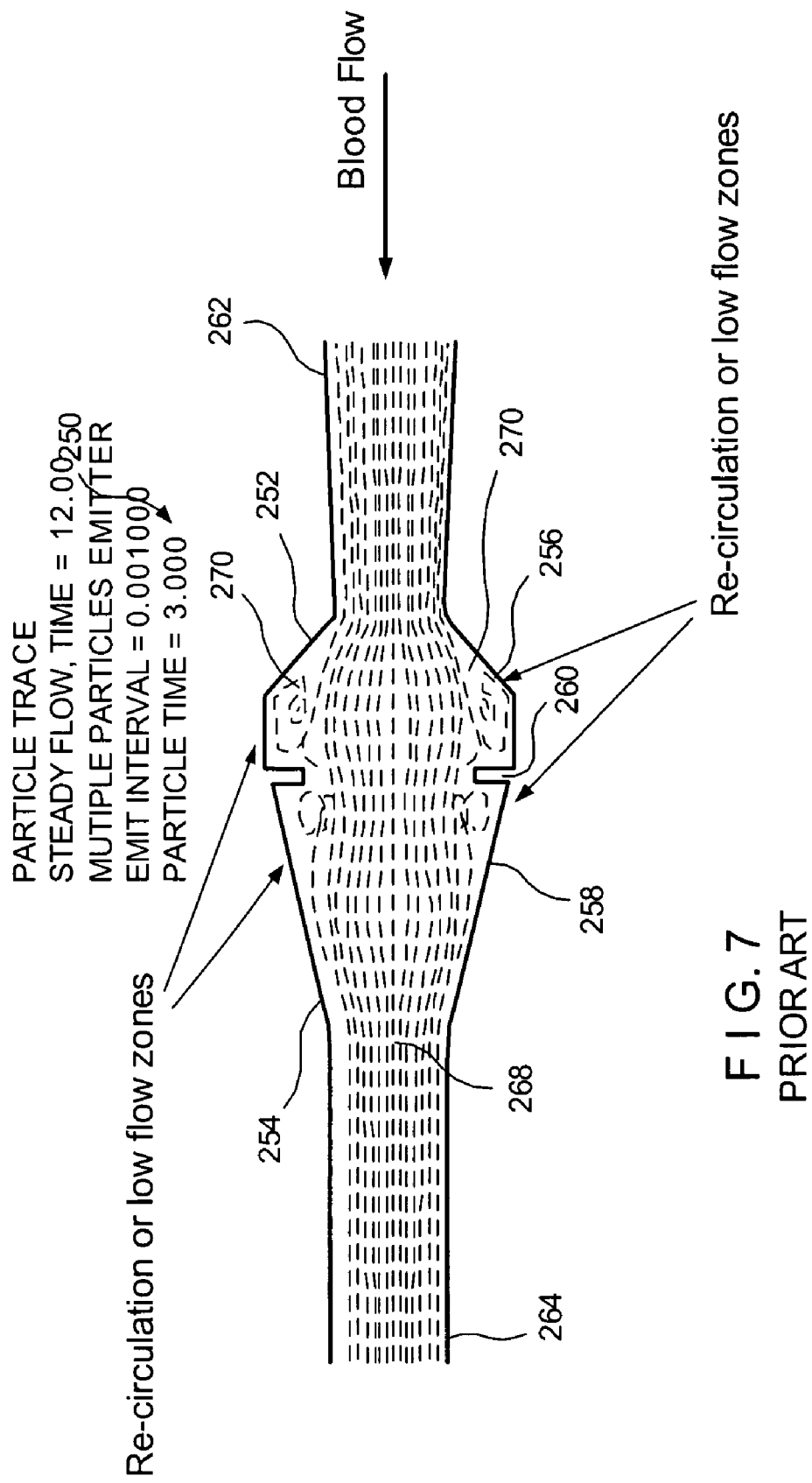
FIG. 7 is a diagram showing the flow through a conventional valve housing.

Another problem that may occur in conventional PASV's is that some blood cells may be damaged by the passage through the slitted membranes at high flow rates. More specifically, areas of flow separation in the valve housing may cause some of the blood to recirculate within the housing, and may cause loss of patency and hemolysis, or the damage of red blood cells. Extended residence time of the blood in the valve may also promote the formation of deposits, or thrombi, which may break off and become lodged in the patient's blood vessels. As shown in FIG. 7, a conventional PASV housing 250 comprises a relatively short luer housing 252 and a barb housing 254. A slitted membrane 260 is located between the two housings 252, 254. When in the open configuration membrane 260 allows the blood to flow through the valve housing 250. For example, the flow of blood may enter the valve body 250 from a line 264 which is connected to a dialysis machine. The blood may leave the valve through a patient line 264, which may be connected to the a catheter leading to the patient.

As shown in FIG. 7, the conventional design of the valve body 250 causes separation of the flow of blood where the walls of the housing diverge sharply from the flow direction. For example, areas of recirculation 256 are formed when the flow of blood separates from walls 270 of the luer housing 252. Another area of recirculation 258 is formed downstream from the slitted membrane 260, in the barb housing 254. Both areas of recirculation 256 and 258 can cause damage to the red blood cells, and increase the residence time of the blood in the valve 250. For a typical blood flow condition through the valve 270, the longest residence time of a blood cell traveling through the recirculation zone may be about two seconds. The velocity of the blood particles in the recirculation areas of the conventional valve 250 is about 26 times slower than the velocity in the core flow region 268.

Figure 9:
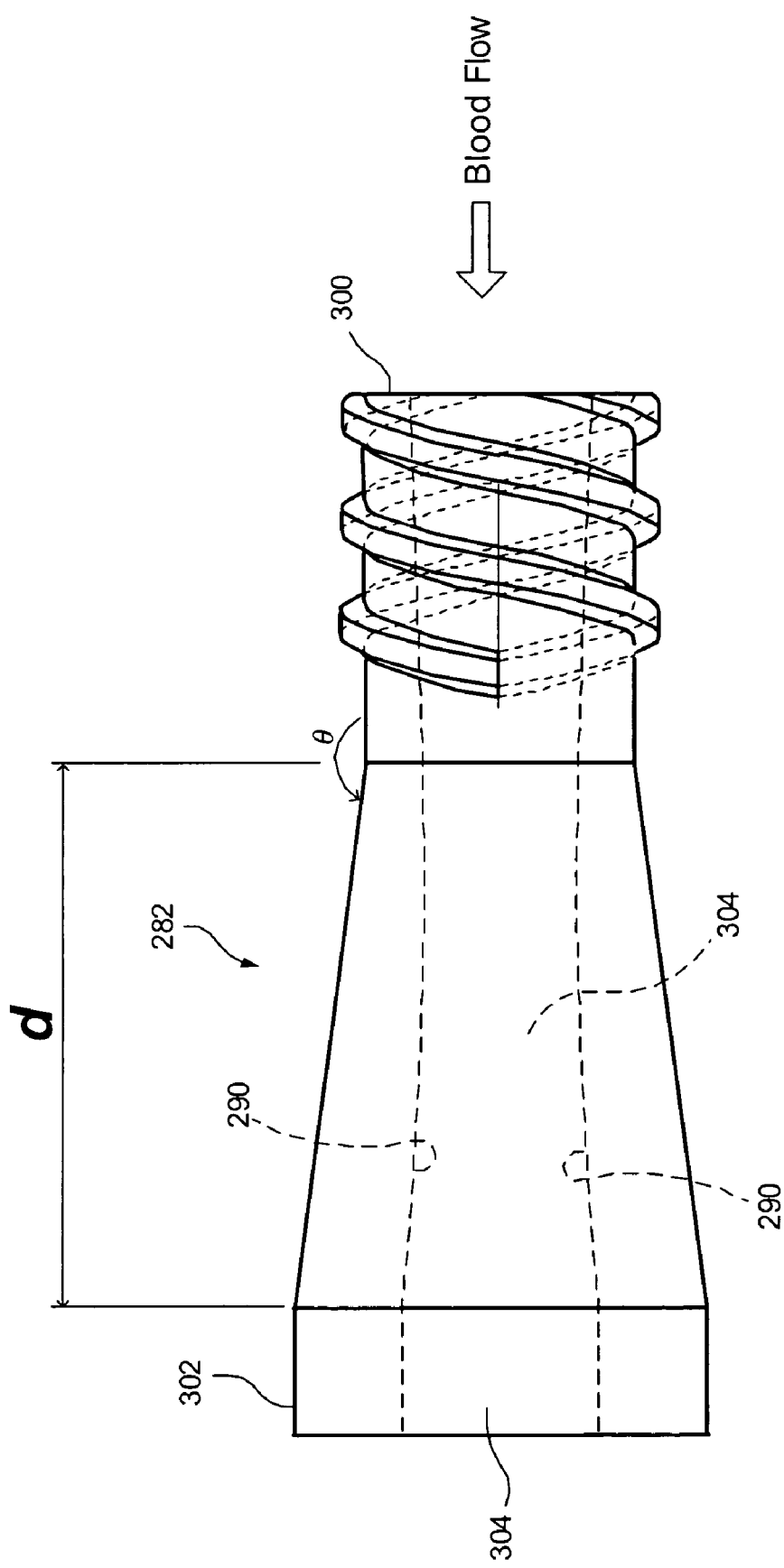
FIG. 9 is a side elevation view showing a luer housing according to an embodiment of the present invention.
Figure 10:
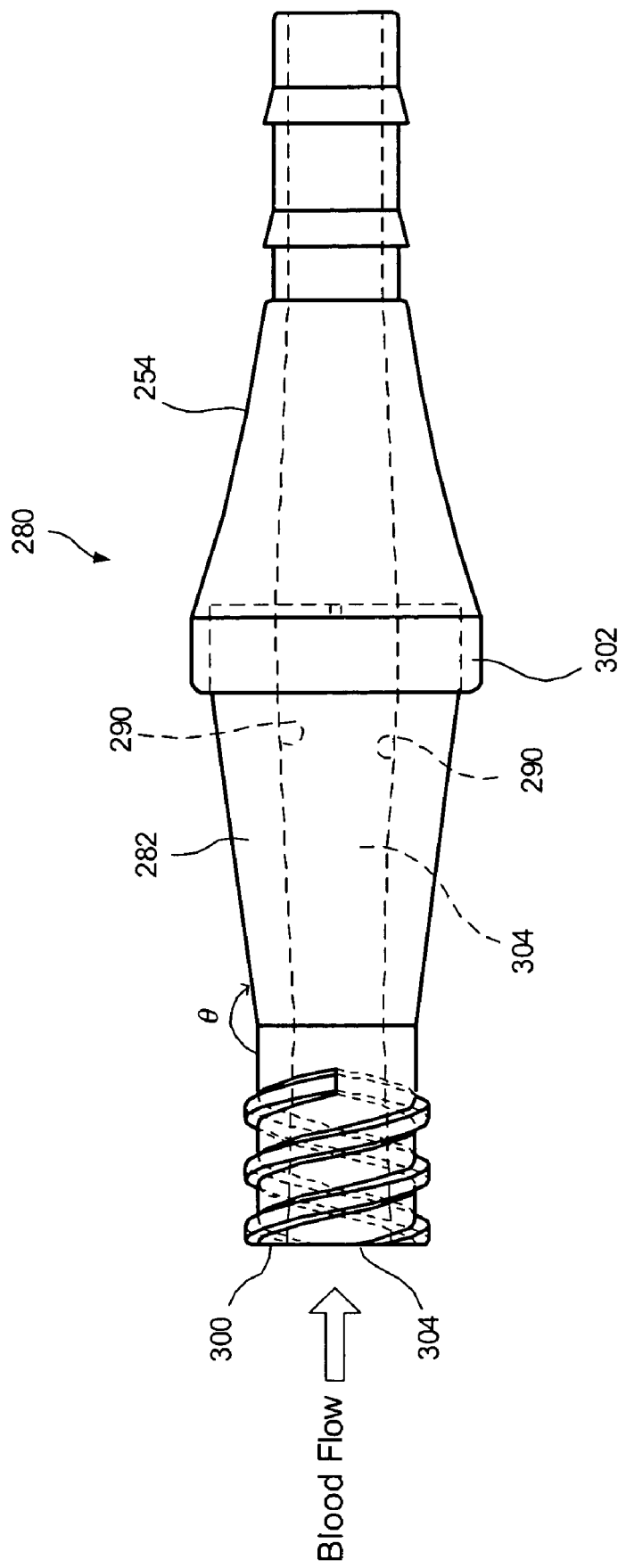
FIG. 10 is a side elevation view showing a luer housing assembled in a valve according to the present invention.

According to exemplary embodiments of the present invention, the areas of recirculation in the PASV may be reduced by constructing the luer and/or barb housings so that flow separation does not occur. For example, as shown in FIGS. 9 and 10, the luer housing 282 of the valve body 280 is designed to provide a smooth transition of the inner wall from the inlet 300, which has a small diameter, to the connection portion 302, which has a larger diameter. Inner wall 290 does not diverge sharply from the inner wall of the inlet portion 300, which is of substantially uniform diameter. Instead, the shape of the flow passage 304 is such that the blood flowing therein minimally separates from the inner wall 290. The formation of the recirculation regions that are common in the conventional design is thus substantially reduced. In an exemplary embodiment, the inner wall 290 is formed with a taper angle θ of between about 125 degrees and about 173 degrees. The length d of the taper section may also be selected to reduce separation of the flow from inner wall 290. For example, the taper length d may be of about 0.525 inches+/−0.200 inches.

Figure 8:
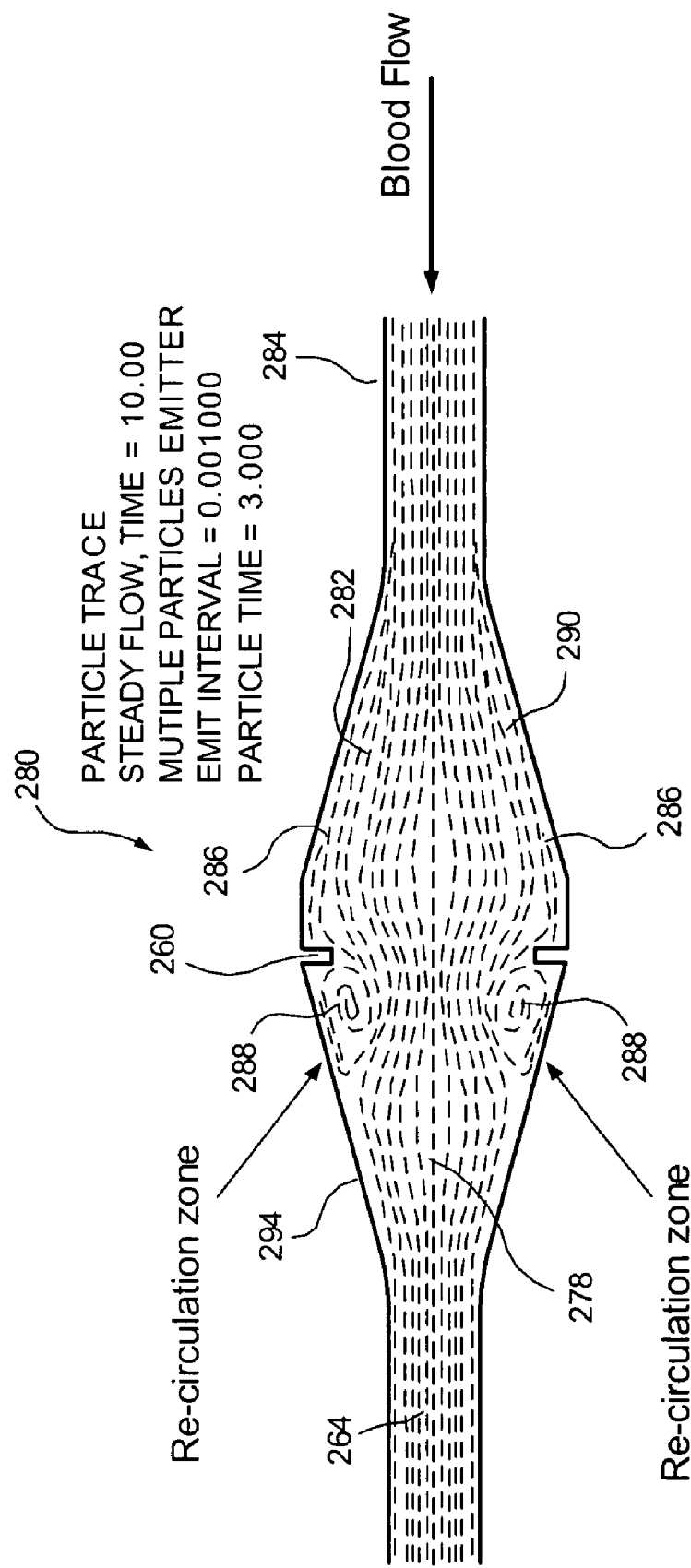
FIG. 8 is a diagram showing the flow through a valve housing according to an embodiment of the present invention.

FIG. 8 shows the flow field under a typical operating configuration of a valve body 280 according to an exemplary embodiment of the invention. The flow of blood enters the valve body 280 from an inlet line through the luer housing 282. Due to the controlled taper of the inner wall 290, the zones of recirculation 286 have almost completely disappeared. The recirculation zones 288 downstream of the slitted membrane have been substantially reduced in strength, resulting in a reduced residence time of the blood in the valve body 280, and in less probability of damage to the red cells. In one exemplary flow condition representative of the operative environment of the valve body 280, the flow velocity in the low flow regions 288 is only about 8 times slower than the velocity of the flow in the core region 278. The residence time of the blood cells going through the low flow areas 288 is reduced to approximately one second, compared to about two seconds for the conventional design.

As described above, various configurations of the slitted membranes used in the PASV according to the present invention may be used to control and direct the flow of fluid through the valve 280. For example, the shape and orientation of the slit(s) may be used to direct the flow of blood towards areas of low flow or recirculation, to complement the effect of the tapered luer housing wall described above. One or more slitted membranes such as the membranes 120, 122 described in FIG. 5 may be used as the flow control elements of the valve body 280. In addition, the tapered luer housing 282 may be used in conjunction with any of the devices described above for directing the flow of fluid towards the slit(s) of the flow control membranes. A PASV valve body encompassing the various benefits of the improvements described above may thus be designed, to address various requirements dictated by the type of medical procedure being performed.

The present invention has been described with reference to specific embodiments, more specifically to a pressure activated safety valve used in a blood dialysis catheter. However, other embodiments may be devised that are applicable to other medical devices, without departing from the scope of the invention. Accordingly, various modifications and changes may be made to the embodiments without departing from the broadest spirit and scope of the present invention as set forth in the claims that follow. The specification and drawings are accordingly to be regarded in an illustrative rather than a restrictive sense.

What is claimed is:

1. A valve assembly for vascular access, comprising:
a body defining a lumen adapted for flowing blood, the body including a luer housing for connection with a first blood conduit and a barb housing for connection with a barb connector; and
a plurality of slitted membranes disposed within the body, each of the slitted membranes generating a partial pressure drop, each of the partial pressure drops being smaller than a total pressure drop through the body portion,
wherein each of the plurality of slitted membranes is separated by a space from the other slitted membrane or membranes, and a first cross-sectional area of the lumen within the space between the membranes is substantially constant, and a second and a third cross-sectional areas of the lumen outside of the space between the membranes have a taper on both sides of the membranes, from a maximum near the membranes to a minimum distant from the membranes, and wherein the first cross-sectional area is less than the second and the third cross-sectional areas.

2. The valve assembly according to claim 1, wherein each of the slitted membranes prevents blood from flowing therethrough when a pressure exerted on each the slitted membranes is less than a corresponding threshold pressure for each of the membranes.

3. The valve assembly according to claim 1, wherein each of the slitted membranes includes a slit formed therein oriented to induce rotation of a flow of blood therethrough.

4. The valve assembly according to claim 3, wherein the slit of a first one of the membranes is offset from the slit of a second one for the membranes by a selected angular distance.

5. The valve assembly according to claim 4, wherein the selected angular distance is approximately 90 degrees.

6. The valve assembly according to claim 1, wherein each of the slitted membranes defines a slit extending therethrough, each slit having a length selected to provide, when in an open configuration, at least a desired minimum flow area therethrough.

7. The valve assembly according to claim 1, wherein each of the slitted membranes has a thickness selected to provide at least a desired minimum flow area therethrough when in an open configuration.

8. The valve assembly according to claim 1, wherein the body further comprises a midsection housing disposed between the luer portion and the barb housing, the midsection housing having a flow passage adapted to align a flow of blood with slits of each of the slitted membranes.

9. The valve assembly according to claim 1, wherein each of the slitted membranes is beveled to direct a flow of blood to a slit formed in a membrane downstream thereof.

10. The valve assembly according to claim 1, wherein a first one of the slitted membranes comprises one of a horizontal slit, a Y-shaped slit, an H-shaped slit, an S-shaped slit, and a partially radial slit.

* * * * *